United States Patent [19]

Barry, Jr.

[11] Patent Number: 5,250,708
[45] Date of Patent: Oct. 5, 1993

[54] POLY(OXYALKYLENE) SUBSTITUTED AMINOPHENOL INTERMEDIATE AND XANTHENE COLORANT

[75] Inventor: Carey N. Barry, Jr., Spartanburg, S.C.

[73] Assignee: Milliken Research Corporation, Spartanburg, S.C.

[21] Appl. No.: 744,253

[22] Filed: Aug. 13, 1991

[51] Int. Cl.$^5$ .......................................... C07D 311/82
[52] U.S. Cl. ..................................... 549/226; 549/227; 549/419; 549/225; 564/305; 564/442; 564/443
[58] Field of Search ...................... 549/226, 227, 419; 564/305, 442, 443

[56] References Cited

U.S. PATENT DOCUMENTS

| | | | |
|---|---|---|---|
| 3,157,633 | 11/1964 | Kuhn | 260/200 |
| 3,769,302 | 10/1973 | Hoover et al. | 260/335 |
| 3,873,573 | 3/1975 | Farber et al. | 260/343.4 |
| 4,144,028 | 3/1979 | Hauser et al. | 8/164 |
| 4,156,682 | 5/1979 | Hotta et al. | 549/226 |
| 4,167,510 | 9/1979 | Brendle | 260/174 |
| 4,302,393 | 11/1981 | Garner et al. | 549/226 |
| 4,330,473 | 5/1982 | Hatano et al. | 549/226 |
| 4,557,862 | 12/1985 | Manget et al. | 549/227 |
| 4,603,202 | 7/1986 | Mayer et al. | 549/226 |
| 4,694,088 | 9/1987 | Kaneko et al. | 549/226 |
| 4,749,796 | 6/1988 | Sensui et al. | 549/227 |
| 4,806,657 | 2/1989 | Zink | 549/226 |
| 4,895,961 | 1/1990 | Schmeidl | 549/227 |
| 4,935,059 | 6/1990 | Mayer et al. | 549/227 |
| 4,945,176 | 7/1990 | Hammond et al. | 549/227 |
| 4,977,278 | 12/1990 | Schmeidl | 549/227 |

FOREIGN PATENT DOCUMENTS

| | | | |
|---|---|---|---|
| 35688 | 9/1977 | Japan | 549/226 |
| 8096588 | 6/1983 | Japan | 549/226 |
| 9120654 | 7/1984 | Japan | 549/226 |
| 9157153 | 9/1984 | Japan | 549/226 |

OTHER PUBLICATIONS

Color Index, 3rd Ed., vol. 4, pp. 4419–4422 (1971).
Venkataraman, *The Chemistry of Synthetic Dyes*, vol. 2, pp. 750–754 (1952).

*Primary Examiner*—Cecilia Tsang
*Attorney, Agent, or Firm*—Timothy J. Monahan; Terry T. Moyer

[57] ABSTRACT

A poly(oxyalkylene) substituted xanthene colorant is providing having the following structure:

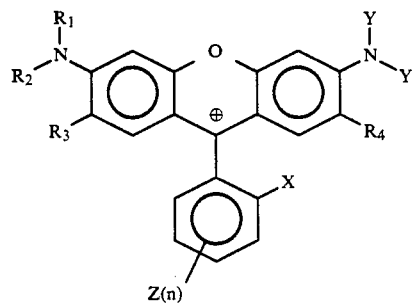

where Y is a poly(oxyalkylene) substituent having a straight or branched polymer chain of from 3 to 400 monomer units selected from ethylene oxide, propylene oxide, butylene oxide and glycidol;

$R_1$ and $R_2$ are independently selected from H, C1-C8 alkyl, aryl and Y, provided that if either $R_1$ or $R_2$ are Y, the other is not H;

$R_3$ and $R_4$ are independently selected from H, C1-C4 alkyl, C1-C4 alkoxy, Cl, Br and I;

X is selected from H, $SO_3-$, $CO_2-$ and $COOR_5$, where $R_5$ is C1-C4 alkyl or aryl; and each Z is independently selected from $SO_3-$, $CO_2-$, $COOR_6$, Cl, and OH, where $R_6$ is C1-C4 alkyl or aryl, and n is 0, 1, 2 or 3.

The colorant is synthesized using a novel poly(oxyalkylene) substituted aminophenol intermediate.

30 Claims, No Drawings

POLY(OXYALKYLENE) SUBSTITUTED AMINOPHENOL INTERMEDIATE AND XANTHENE COLORANT

BACKGROUND OF THE INVENTION

This invention relates to a novel poly(oxyalkylene) substituted aminophenol compound which is useful in the manufacture of xanthene colorants, particularly triphenylmethane derivatives such as rhodamines. The xanthene colorants exhibit improved water solubility and fugitivity.

Xanthene dyes, and in particular rhodamine dyes, are well known in the art as exemplified in the COLOR INDEX, 3rd. ed., Vol. 4 , pp. 4419–4422 (1971). These dyes range from bright red to bright bluish red, and typically fluoresce orange or red upon exposure to ultraviolet light. Rhodamine dyes have found use in a variety of applications including coloring soaps and other cleaning products, water tracing and leak detection. While the dyes have gained wide acceptance throughout the industry, they have come under suspicion as being toxic and unsuitable for use when human exposure to the dye is expected. Less toxic rhodamines have been commercialized, such as Rhodamine WT. However, Rhodamine WT has relatively poor light fastness, and tends to stain skin, clothes and equipment.

Another category of triphenylmethane type xanthene dyes is exemplified by the fluoran compounds disclosed in Farber et al., U.S. Pat. No. 3,873,573; Hatano et al., U.S. Pat. No. 4,330,473; and Zink, U.S. Pat. No. 4,806,657. The compounds are diamino-xanthene dyes having amino groups in the 3- and 7-positions. In particular, the amino group in the 7- position may be phenyl substituted. The patents also disclose p-methoxy-N-phenylaniline intermediates which may be reacted with a ketonic acid. These dyes are particularly useful as recording material, since opening the lactone ring of such compounds converts the faintly colored material to a dark green or black color.

Methods of improving the water solubiltiy or fugitivity of dyes by providing one or more poly(oxyalkylene) substituents is known in the art. Examples of "fugitive tints" are disclosed in Kuhn, U.S. Pat. No. 3,157,633; Hauser et al., U.S. Pat. No. 4,144,028; and Brendle, U.S. Pat. No. 4,167,510. The aforementioned colorants have been found to be especially useful in the textile industry for identification of fibers and yarn during weaving or tufting. The colorants are easily removed to allow the textile product to be dyed a uniform color in subsequent stages of the manufacturing process. A large number of organic dyes have been synthesized with intermediates provided with poly(oxyalkylene) substituents and include azo, methine, anthraquinone and some triphenylmethane colorants. Nevertheless, attempts to synthesize poly(oxyalkylene) substituted xanthene dyes have not heretofore met with success.

Typical prior art processes for manufacturing rhodamine dyes provide for condensing m-dialkylaminophenol with phthalic anhydride. A diagram of the synthesis of Rhodamine B, described in Venkataraman, THE CHEMISTRY OF SYNTHETIC DYES, Vol. II, pp. 750–54 (1952), is set forth below.

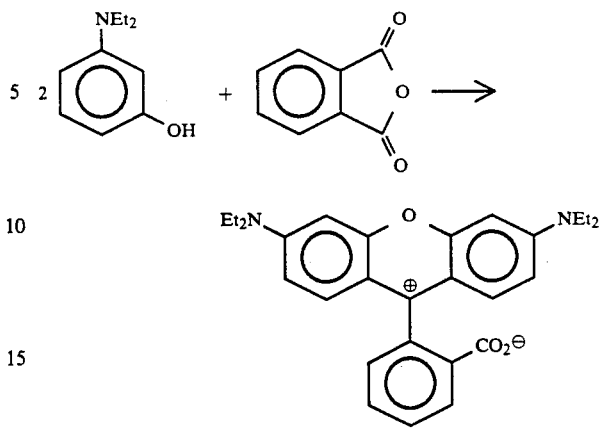

In synthesizing a poly(oxyalkylene) substituted colorant, it is desirable to alkoxylate one or more of the reactants or intermediates which form the colorant. However, the intermediates used in a typical rhodamine synthesis may not be readily alkoxylated without adding poly(oxylakylene) to sites on the intermediate which participate in colorant formation. Thus, despite a strong desire to provide a poly(oxyalkylene) substituted rhodamine colorant or other poly(oxyalkylene) substituted triphenylmethane type xanthene colorants to the market, such a product has not been available.

SUMMARY OF THE INVENTION

Therefore, one of the objects of the invention is to provide a poly(oxyalkylene) substituted xanthene colorant.

Another object of this invention is to provide a synthesis route for a xanthene colorant wherein at least one of the reactants may be substituted with a poly(oxyalkylene) group.

Still another object of the invention is to provide a poly(oxyalkylene)aminophenol intermediate for use in the manufacture of xanthene colorants, particularly rhodamine colorants.

Accordingly, an aminophenol is provided which is useful as an intermediate in the manufacture of a xanthene colorant. The amino group of said aminophenol is di-substituted with a poly(oxyalkylene) substituent having a straight or branched polymer chain of at least 2 monomer units selected from ethylene oxide, propylene oxide, butylene oxide and glycidol. In one embodiment, at least one mole of the poly(oxyalkylene) substituted m-aminophenol is reacted with phthalic anhydride or other aromatic compound having an aldehyde functionality available. A second mole of poly(oxyalkylene) substituted m-aminophenol may also be provided to form a rhodamine colorant. Alternatively, a non-polymeric aminophenol reactant, such as N,N-diethyl-m-aminophenol or N-aryl-p-aminophenol, may be employed. Use of the latter reactant results in a black, or dark green, xanthene colorant rather than a rhodamine. The invention herein also provides for synthesis of a black, or dark green, xanthene colorant using one mole of N,N-bis(poly(oxyalkylene))-p-aminophenol with one mole of a polymeric or non-polymeric m-aminophenol. It is envisioned that reactants having various substituent groups, in addition to poly(oxyalkylene), may be employed without deviating from the spirit of the invention.

This novel intermediate has the advantage being useful in the traditional route of xanthene synthesis, i.e. the condensation reaction of an aminophenol and phthalic anhydride. The poly(oxyalkylene) xanthene colorant features very good water solubility and fugitivity, and is believed to be relatively nontoxic. The rhodamine colorants disclosed herein show good lightfastness relative to Rhodamine WT.

DESCRIPTION OF THE PREFERRED EMBODIMENT OF THE INVENTION

Without limiting the scope of the invention, the preferred features of the invention are hereinafter set forth.

The rhodamine colorant embodiment of the present invention is a product of a condensation reaction utilizing an N,N-bis(poly(oxyalkylene))-m-aminophenol intermediate. The intermediate may be characterized by the following formula:

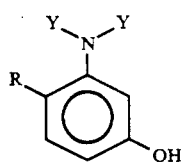

where Y is a poly(oxyalkylene) substituent and R may be H, C1–C4 alkyl, C1–C4 alkoxy, Cl, Br, and I. Preferably R is H, methyl, ethyl, Cl, Br or I. In a more preferred embodiment, the N,N-bis(poly(oxyalkylene))-m-aminophenol intermediate is substituted with methyl or ethyl, or is unsubstituted, i.e. R is H.

The intermediate is prepared from m-acetamidophenol or p-acetamidophenol which is reacted with 2,3-dihydropyran in the presence of pyridinium p-toluenesulfonate to protect the phenol. Next, the acetamido group is removed by heating the compound in a solution containing sodium hydroxide to make the amine group of the compound available for alkoxylation. Details of the foregoing procedures are set forth in Examples 1 and 2 using m-acetamidophenol as the starting material.

EXAMPLE 1

Synthesis of Protected m-acetamidophenol

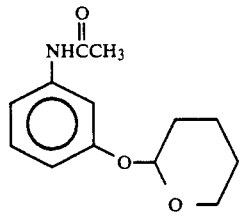

2,3-Dihydropyran (160 mL) was added slowly to a stirring mixture of m-acetamidophenol (151.2 g) and pyridinium p-toluenesulfonate (5.0 g) in dichloromethane (1.2 L) at ambient temperature and under a nitrogen atmosphere. The resulting mixture was stirred at ambient temperature for about 16 hours and washed with dilute aqueous NaOH (4×350 mL, pH=11). Rotary evaporation of the organic solution afforded the protected phenol as a white crystalline solid (98% purity by HPLC analysis).

EXAMPLE 2

Selective Removal of Acetamido Protecting Group

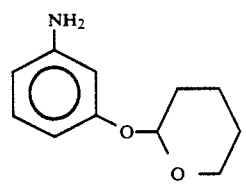

The product of Example 1 (235 g) was added to a mixture of sodium hydroxide (100 g), water (135 mL) and ethylene glycol (400 mL). The resulting mixture was heated at 130° C. for 4 hours. After cooling to ambient temperature, the mixture was diluted with water (450 mL) and extracted with dichloromethane (4×350 mL). The combined organic extracts were back extracted with dilute aqueous NaOH (4×300 mL, pH=11), dried over anhydrous potassium carbonate and concentrated to a yellow oil by rotary evaporation (about 94% purity by HPLC; $^1$H NMR consistent with desired product).

The product of Example 2 may be alkoxylated to add poly(oxyalkylene) substituents to the amine group using standard techniques. Monomer units selected from glycidol, ethylene oxide, propylene oxide and butylene oxide may be employed as reactants. In a preferred embodiment, each of said poly(oxyalkylene) substituents is comprised of from 3 to 400 of such monomer units, more preferably 3 to 250. Additionally, water solubility and fugitivity is enhanced by providing that at least 75% of the monomer units be ethylene oxide. Monomer units selected from ethylene oxide, propylene oxide and glycidol are preferred both from considerations of cost and performance.

Another consideration for improved performance of the rhodamine colorant is the branching of the poly(oxyalkylene substituent. Glycidol ma be incorporated into the polymer to provide multiple hydroxyl sites for chain growth. It is believed that adding glycidol first to the amino group optimizes branching. More uniform branching of the poly(oxyalkylene) substituent may be achieved by reacting a "secondary hydroxyl" forming epoxide, such as propylene oxide, with the glycidol, followed by addition of ethylene oxide. A glycidol equivalent may be provided by reacting chloropropanediol with the amino group of the product of Example 2. Two moles of chloropropanediol may be reacted with the amine group without substantial difficulty. If additional branched alkylene oxide units are desired, glycidol can be added to the poly(oxyalkylene) chain.

The terminal group on each poly(oxyalkylene) chain is not chemically bound in the xanthene colorant and is not believed to participate in formation of the colorant compound. Therefore, the precise identity of the terminal group is not deemed to be critical to the invention. However, by way of example and not limitation, the following terminal groups may be employed:

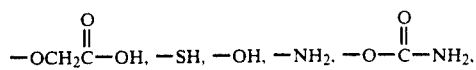

-continued

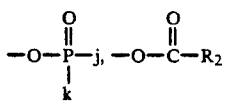

and sulfonates and sulfates of each of the members of said group, wherein $R_2$ is H, an alkyl radical containing up to about 20 carbon atoms or carboxy-terminated alkyl radical containing up to about 20 carbon atoms, j and k are OH, OM or $OR_3$ wherein M is a cation moiety of an alkali metal, an alkaline earth metal, transition metal, e.g., nickel, etc. or ammonium, and $R_3$ is an alkyl radical containing up to about 20 carbon atoms.

Even if the terminal group of the poly(oxyalkylene) substituent is found to be reactive with, for example, phthalic anhydride reactant, this can be overcome by providing an excess of phthalic anhydride during the formation of the colorant. The phthalic anhydride group can be removed later under acidic or basic conditions.

An example of the addition of ethylene oxide to the product of Example 2 is set forth in Example 3 below.

EXAMPLE 3

Synthesis of O-protected N,N-bis(hydroxyethylpolyoxyethylene)-m-aminophenol

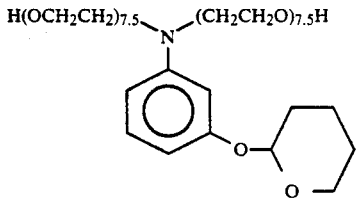

The product of Example 2 (250 g) is treated with 2.5 g of KOH and eight hundred sixty grams of ethylene oxide were added to the reactor in the usual fashion. The product was vacuum stripped and removed from the reactor giving a final hydroxyl number of 132 which compares favorably with a theoretical hydroxyl number of 131. The number of oxyethylene groups shown represents an average.

The product of Example 3 can be converted to the desired intermediate by treatment with acid in a methanol solution as shown in the following example.

EXAMPLE 4

Synthesis of N,N-bis(hydroxyethylpolyoxyethylene)-m-aminophenol

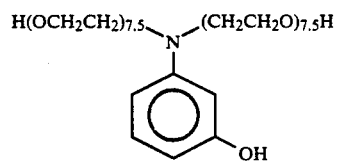

Concentrated hydrochloric acid (16.5 mL) was added in a continuous stream to a solution of the product of Example 3 (85.0 g) and sodium bisulfite (46.6 g) in water (220 mL) The resulting mixture was stirred at ambient temperature for about 18 hours and extracted with dichloromethane (4×200 mL). The combined extracts were washed with a 50/50 mixture of saturated sodium chloride and saturated sodium bicarbonate (2×200 mL) and dried over anhydrous potassium carbonate. The mixture was filtered and the organic solution vacuum stripped to give 83 g of a light brown oil. Product identification was established by $^1$H NMR analysis.

While the foregoing examples employ m-acetamidophenol as the starting material, substituted m-acetamidophenols may be similarly treated, provided that the substituent groups are selected to avoid interaction during synthesis of the N,N-bis(poly(oxyalkylene))-m-aminophenol intermediate. For example, intermediates having the following structure are suitable for use in making a poly(oxyalkylene) substituted rhodamine colorant.

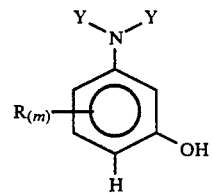

wherein Y is a poly(oxyalkylene) substituent as defined above, and R is selected from C1-C4 alkyl, C1-C4 alkoxy, Cl, Br, and I, and m is 0, 1, 2 or 3, preferably R is methyl or ethyl and m is 0 or 1.

The rhodamine colorant herein may be made by reacting two moles of the N,N-bis(poly(oxyalkylene))-m-aminophenol intermediate with phthalic anhydride as shown in the following example.

EXAMPLE 5

Synthesis of a Polymeric Fluorescent Red Containing 30 EO monomers

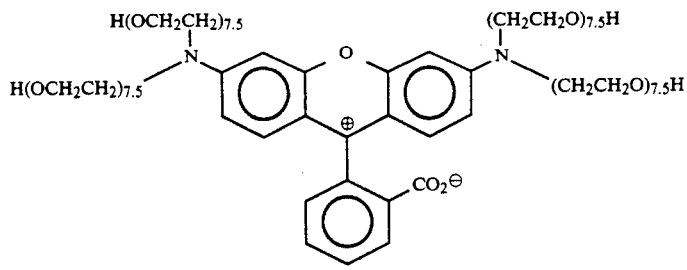

A mixture of the product of Example 4 (77.7 g) and phthalic anhydride (7.41 g) was heated under a nitrogen atmosphere to 200° C. and immediately cooled to 100° C. The mixture was heated at 100° C. for 2 hours. Additional phthalic anhydride (3.7 g) was added and the mixture heated for 16 hours at 100° C. Following the addition of 78% sulfuric acid (0.8 g) the mixture was heated at 175°-190° C. for 3 hours. Phthalic anhydride (11.11 g) was charged to the reactor and heating continued for 3 hours. Phthalic anhydride (11.11 g) was again charged to the reactor and heating continued for 6 hours. A final charge of phthalic anhydride (16.67 g) was added and heating at 130° C. was continued for 16 hours. The mixture was cooled below 100° C. and treated with 150 mL of water. The aqueous mixture was heated at reflux for about 16 hours. After settling for several minutes the hot mixture separated into two layers and the upper aqueous layer was decanted. The product was washed with hot water (400 mL) by stirring for several minutes at 80° C. After settling for several more minutes, the upper aqueous layer was removed by decanting. This wash procedure was repeated three times. Residual water was removed by rotary evaporation affording a red colorant with an absorptivity of 17.5 at 550 nm.

As noted at the onset, a rhodamine colorant having improved water solubility, fugitivity and light fastness can be obtained with a single mole of N,N-bis(poly(oxyalkylene))-m-aminophenol intermediate incorporated into the colorant structure. A variety of m-aminophenols such as N-alkyl-m-aminophenol, N,N-dialkyl-m-aminophenol and N-aryl-m-aminophenol may constitute the colorant in addition to the N,N-bis(poly(oxyalkylene))-m-aminophenol. By way of further example, the amino group may be mono- or di-substituted with C1-C20 alkyl or aryl, preferably, C1-C8 alkyl or aryl. The N,N-bis(poly(oxyalkylene))-m-aminophenol, referred to herein as polymeric M-aminophenol, and a non-polymeric m-aminophenol may be reacted with phthalic anhydride in either order. Thus, for example, one mole of non-polymeric N,N-dialkyl-m-aminophenol could be reacted with one mole of phthalic anhydride according to the procedure disclosed in Hoover, et al., U.S. Pat. No. 3,769,302, Example A. Next, the intermediate is reacted with an equamolar amount of N,N-bis(poly(oxyalkylene))-m-aminophenol.

While phthalic anhydride is a common reactant for rhodamine synthesis, there are a variety of compounds which can be employed in the present invention in its place, particularly benzaldehyde. Additionally, by way of example and not limitation, the following compounds may be substituted for phthalic anhydride or benzaldehyde, referred to generally herein as phthalic anhydride or benzaldehyde derivatives, in the synthesis of rhodamine colorants:

o-formyulbenzenesulfonic acid;
4-formyl-1,3-benzenedisulfonic acid;
o-formylbenzoic acid;
o-formyl alkylbenzoates;
mono, di and tri-halobenzaldehydes with Cl, Br and I; Cl is preferred, such as o-chlorobenzaldehyde;
mono, di, tri and tetra-halophthalic anhydride with Cl, Br and I;
trimellitic acid; and
5-hydroxytrimellitic acid.

If a benzaldehyde or benzaldehyde derivative is employed in the synthesis of a colorant, a second oxidation step is performed to oxidize the triphenyl substituted carbon. Suitable oxidizing agents include persulfate, dichromate, peroxides and benzoquinones.

Thus, rhodamine colorants having the following general structure may be produced according to the teachings herein:

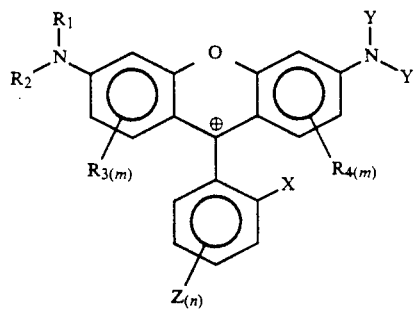

where Y is a poly(oxyalkylene) substituent as defined above; $R_1$ and $R_2$ are independently selected from H, C1-C20 alkyl, aryl and Y, provided that if either $R_1$ or $R_2$ are Y, the other is not H; $R_3$ and $R_4$ are independently selected from H, C1-C4 alkyl, C1-C4 alkoxy, Cl, Br and I, m is 0, 1, 2 or 3; X is selected from H, $SO_3-$, $CO_2-$, $COOR_5$, Cl, Br and OH, and $R_5$ is C1-C8 alkyl or aryl; each Z is independently selected from $SO_3-$, $CO_2-$, $COOR_6$, Cl, Br and OH, and $R_6$ is C1-C8 alkyl or aryl, and n is 0, 1, 2 or 3. In a preferred embodiment of the rhodamine colorant, X is H, $CO_2-$, $SO_3-$, Cl or $COOR_5$ where $R_5$ is C1-C4 alkyl or aryl; and Z is $CO_2-$, $SO_3-$, OH, Cl and $COOR_6$ where $R_6$ is C1-C4 alkyl or aryl, and n is 0, 1 or 2. Most preferred are colorants in which X is $CO_2-$, $SO_3-$ or $COOR_5$ where $R_5$ is C1-C4 alkyl or aryl; and n is 0.

EXAMPLE 6

Multi-fabric Fugitivity Testing

A test was constructed to determine the fugitivity or washablity of colorants included in the present invention relative to prior art rhodamine dyes on a variety of fabrics. Thirteen fabric test strips made from acetate, Self-Extinguishing Monoacrylic (SEF), Arnel, bleached cotton, Creslan 61, Dacron 54, Dacron 64, Nylon 6.6, Orlon 75, Spun Silk, polypropylene, viscose, and wool were treated with dilutions of rhodamine dyes or colorants. In each case the tint solution was diluted to the same absorptivity level. The fabric test strips were then allowed to dry and then they were rinsed in cold water. A number rating on a five point scale was given depending on how closely the fabric returned to its untreated color. The ratings were obtained using a Hunter Labscan Colorimeter. The ratings are shown in Table 1. A rating of 5 indicates complete fugitivity or washability, and a rating of 0 indicates complete staining. The structures of the tints tested are provided below. Rhodamine WT is a commercially available rhodamine dye from Chromatech Inc., Plymouth, Mich., U.S.A.; the precise structure is unknown. Rhodamine Colorant I is the product of Example 5.

TABLE 1

| FIBER | RHODAMINE WT | RHODAMINE B | COLORANT 1 |
| --- | --- | --- | --- |
| ACETATE | 2.54 | 4.55 | 4.81 |
| SEF | 0.10 | 3.32 | 3.80 |
| ARNEL | 2.03 | 4.04 | 4.02 |
| COTTON | 0.63 | 1.92 | 3.45 |
| CRESLAN 61 | 1.89 | 4.29 | 4.57 |
| DACRON 54 | 1.26 | 4.10 | 4.62 |
| DACRON 64 | 1.14 | 3.10 | 3.30 |
| NYLON 6.6 | 1.57 | 3.37 | 4.48 |
| ORLON 75 | 0.87 | 4.01 | 4.45 |
| SPUN SILK | 0.00 | 0.00 | 0.62 |
| POLYPROPYLENE | 0.78 | 3.04 | 4.03 |
| VISCOSE | 0.81 | 2.02 | 2.16 |
| WOOL | 0.00 | 0.00 | 3.37 |

The data shown above clearly demonstrates that the colorant of the current invention is more washable from the majority of fibers than either Rhodamine WT or Rhodamine B. Colorant I outperformed Rhodamine B or 11 of 12 fabrics. Rhodamine WT was the least washable of all the colors tested on all of the fabrics.

In an alternate embodiment of the invention, a dark green or black xanthene colorant is prepared by reacting one mole of a m-aminophenol, one mole of a p-aminophenol and phthalic anhydride, benzoldehyde or derivatives thereof. At least one of the aminophenol compounds is di-substituted with poly(oxyalkylene). Suitable N,N-bis(poly(oxyalkylene))-m-aminophenols and their preparation are set out in detail above. Thus, for example, one mole of N,N-bis(poly(oxyalkylene))-m-aminophenol may be reacted with phthalic anhydride according to the procedure disclosed in Hoover, et al., U.S. Pat. No. 3,769,302, Example A. Next, N-phenyl-2-methyl-4-hydroxyaniline is reacted with the adduct of step one to make a colorant. A black xanthene colorant is produced having improved water solubility and fugitivity. A variety of other non polymeric, p-aminophenols may be similarly employed in the invention. By way of further example, the amino group may be mono- or di- substituted with C1-C20 alkyl or aryl, preferably, C1-C8 alkyl or aryl.

Also within the scope of the present invention is to provide a N,N-bis(poly(oxyalkylene))-p-aminophenol intermediate which can be incorporated into the colorant with either a non-polymeric or polymeric m-aminophenol. The N,N-bis(poly(oxyalkylene))-p-aminophenol intermediate may be synthesized according to the procedure outlined in Examples 1–4 using p-acetamidophenol as the starting material. The intermediate may be generally characterized by the formula:

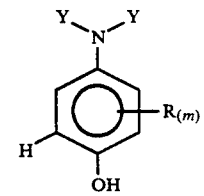

wherein Y is poly(oxyalkylene) substituent as defined above; each R is independently selected from C1–C4 alkyl, C1–C4 alkoxy, Cl, Br and I, and m is 0, 1, 2 or 3. Preferably R is methyl, ethyl, Cl, Br or I. More preferably, R is methyl or ethyl and is positioned meta to the hydroxyl group of the phenol, and m is 0 or 1.

Thus, xanthene colorants having poly(oxyalkylene) substituents may be characterized by the formula:

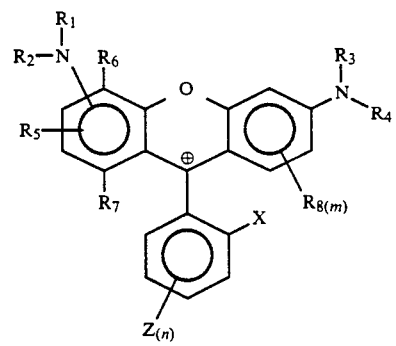

where $R_1$ and $R_2$ are independently selected from H, C1–C20 alkyl and aryl, or are both Y, where Y is a poly(oxyalkylene) substituent defined above;

$R_3$ and $R_4$ are independently selected from H, C1–C20 alkyl and aryl, or are both Y, provided that either $R_1$ and $R_2$ or $R_3$ and $R_4$ are Y;

$R_5$, $R_6$ and $R_7$ are independently selected from H, C1–C4 alkyl, C1–C4 alkoxy, Cl, Br and I;

each $R_8$ is independently selected from C1–C4 alkyl, C1–C4 alkoxy, Cl, Br and I, and m is 0, 1, 2 or 3;

X is selected from H, $SO_3-$, $CO_2-$, $COOR_9$, Cl, Br and OH, and $R_9$ is C1–C8 alkyl or aryl; and each Z is independently selected from $SO_3-$, $CO_2-$, $COOR_{10}$, Cl, Br and OH, and $R_{10}$ is C1–C8 alkyl or aryl; and n is 0, 1, 2 or 3. Preferably, X is selected from H, $CO_2-$, $SO_3-$, Cl and $COOR_9$ where $R_9$ is C1–C4 alkyl or aryl; and each Z is independently selected from $CO_2-$, $SO_3-$, OH–, Cl and $COOR_{10}$ where $R_{10}$ is C1–C4 alkyl or aryl, and n is 0, 1 or 2, and more preferably, X is $CO_2-$, $COOR_9$, or $SO_3-$, and $R_9$ is C1–C4 alkyl or aryl, and n is 0.

There are, of course, many alternate embodiments and modifications which are intended to be included within the scope of the following claims. For example, the colorant of the present invention may be incorporated into a thermoplastic resin as described in Baumgartner et al., U.S. Pat. No. 4,732,570 (incorporated by reference). Alternatively, embodiments of the colorant having reactive terminal groups may be reacted into a thermoplastic polymer as described in Cross et al., U.S. Pat. No. 4,284,729 (incorporated by reference).

What we claim is:

1. A colorant intermediate comprising a compound having the structure:

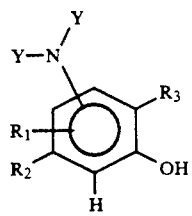

wherein Y is poly(oxyalkylene) substituent having a straight or branched chain of from 3 to 250 monomer units selected from ethylene oxide, propylene oxide, butylene oxide and glycidol;

$R_1$, $R_2$ and $R_3$ are independently selected from H, C1–C4 alkyl, C1–C4 alkoxy, Cl, Br and I.

2. The compound of claim 1 wherein said poly(oxyalkylene) substituents are comprised of monomer units selected from ethylene oxide, propylene oxide and glycidol.

3. The compound of claim 2 wherein at least 75 percent of each of said poly(oxyalkylene) substituents is comprised of said ethylene oxide monomer units.

4. The compound of claim 1 wherein $R_1$, $R_2$ and $R_3$ are independently selected from H, methyl, ethyl, Cl, Br and I.

5. The compound of claim 4 wherein said monomer units are selected from ethylene oxide, propylene oxide and glycidol.

6. The compound of claim 1 wherein $R_1$ is selected from H, methyl and ethyl, and $R_2$ and $R_3$ are H.

7. The compound of claim 6 wherein said monomer units are selected from ethylene oxide, propylene oxide and glycidol.

8. A colorant intermediate comprising a compound having the structure:

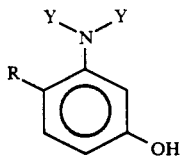

wherein Y is poly(oxyalkylene) substituent having a straight or branched polymer chain of from 3 to 250 monomer units selected from ethylene oxide, propylene oxide, butylene oxide and glycidol; R is H, C1–C4 alkyl, C1–C4 alkoxy, Cl, Br or I.

9. The compound of claim 8 wherein at least 75 percent of each of said poly(oxyalkylene) substituents is comprised of said ethylene oxide monomer units.

10. The compound of claim 8 wherein R is selected from H, methyl and ethyl, Cl, Br and I.

11. The compound of claim 10 wherein at least 75 percent of said poly(oxyalkylene) substituents comprise said ethylene oxide monomer units.

12. The compound of claim 8 wherein R is H, methyl or ethyl, and wherein said poly(oxyalkylene) substituents are comprised of monomer units selected from ethylene oxide, propylene oxide and glycidol.

13. The compound of claim 8 wherein R is H or methyl.

14. The compound of claim 8 wherein R is H.

15. The compound of claim 14 wherein said poly(oxyalkylene) substituents are comprised of monomer units selected from ethylene oxide, propylene oxide and glycidol.

16. A xanthene colorant comprising a compound having the structure:

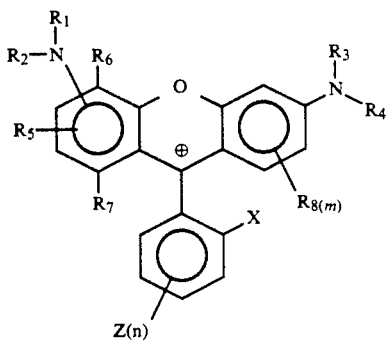

where $R_1$ and $R_2$ are independently selected from H, C1–C20 alkyl and aryl, or are both Y, where Y is a poly(oxyalkylene) substituent having a straight or branched polymer chain of from 3 to 250 monomer units selected from ethylene oxide, propylene oxide, butylene oxide and glycidol;

$R_3$ and $R_4$ are both Y;

$R_5$, $R_6$ and $R_7$ are independently selected from H, C1–C4 alkyl, C1–C4 alkoxy, Cl, Br and I;

each $R_8$ is independently selected from C1–C4 alkyl, C1–C4 alkoxy, Cl, Br and I, and m is 0, 1, 2 or 3;

X is selected from H, $SO_3-$, $CO_2-$, $COOR_9$, Cl, Br and OH, and $R_9$ is C1–C8 alkyl or aryl; and each Z is independently selected from $SO_3-$, $CO_2-$, $COOR_{10}$, Cl, Br and OH, and $R_{10}$ is C1–C8 alkyl or aryl, and n is 0, 1, 2 or 3.

17. The compound of claim 16 wherein at least 75 percent of each of said poly(oxyalkylene) substituents is comprised of said ethylene oxide monomer units.

18. The compound of claim 16 wherein said poly(oxyalkylene) substituents are comprised of monomer units selected from ethylene oxide, propylene oxide and glycidol.

19. The compound of claim 16 wherein X is selected from H, $CO_2-$, $SO_3-$, Cl and $COOR_9$ where $R_9$ is C1–C4 alkyl or aryl; and each Z is independently selected from $CO_2-$, $SO_3-$, OH, Cl and $COOR_{10}$ where $R_{10}$ is C1–C4 alkyl or aryl, and n is 0, 1 or 2.

20. The compound of claim 19 wherein at least 75 percent of each of said poly(oxyalkylene) substituents is comprised of said ethylene oxide monomer units.

21. The compound of claim 19 wherein $R_1$ and $R_2$ are independently selected form H, C1–C8 alkyl and Y;

$R_5$ is H, methyl or ethyl;

$R_6$ and $R_7$ are H; and $R_8$ is methyl or ethyl, and m is 0 or 1.

22. The compound of claim 18 wherein $R_1$ and $R_2$ are selected from H and C1–C8 alkyl.

23. The compound of claim 21 wherein $R_1$ and $R_2$ are H and $R_5$ is meta to the ether linkage of said colorant.

24. A xanthene colorant comprising a compound having the structure:

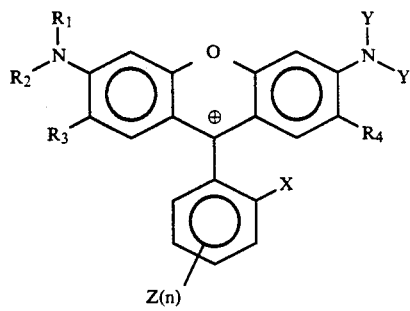

wherein Y is a poly(oxyalkylene) substituent having a straight or branched polymer chain of from 3 to 250 monomer units selected from ethylene oxide, propylene oxide, butylene oxide and glycidol;

$R_1$ and $R_2$ are independently selected from H, C1–C8 alkyl, aryl and Y, provided that if either $R_1$ or $R_2$ are Y, the other is not H;

$R_3$ and $R_4$ are independently selected from H, C1–C4 alkyl, C1–C4 alkoxy, Cl, Br and I;

X is selected from H, $SO_3-$, $CO_2-$ and $COOR_5$, where $R_5$ is C1–C4 alkyl or aryl; and each Z is independently selected from $SO_3-$, $CO_2-$, $COOR_6$, and OH, where $R_6$ is C1–C4 alkyl or aryl, and n is 0, 1, 2 or 3.

25. The compound of claim 24 wherein X is $CO_3-$, $SO_3-$ or $COOR_5$, where $R_5$ is C1–C4 alkyl.

26. The compound of claim 25 wherein said monomer units are selected from ethylene oxide, propylene oxide and glycidol, and wherein at least 75 percent of said monomer units are ethylene oxide.

27. The compound of claim 24 wherein n is 0.

28. The compound of claim 27 wherein $R_1$ and $R_2$ are Y, and $R_3$ and $R_4$ are independently selected from H, methyl and ethyl.

29. The compound of claim 24 wherein X is $CO_2-$, n is 0, and $R_3$ and $R_4$ are H or methyl.

30. The compound of claim 29 wherein said poly(oxyalkylene) substituents are comprised of monomer units selected from ethylene oxide, propylene oxide and glycidol.

* * * * *

UNITED STATES PATENT AND TRADEMARK OFFICE
CERTIFICATE OF CORRECTION

PATENT NO. : 5,250,708
DATED : October 5, 1993
INVENTOR(S) : Carey N. Barry, Jr.

It is certified that error appears in the above-indentified patent and that said Letters Patent is hereby corrected as shown below:

Column 11, line 21, insert the word "polymer" before the word "chain".

Column 12, line 61, the word "form" should be changed to "from".

Column 14, line 6, insert "Cl," before the words "and OH".

Column 14, line 8, "$CO_3$" should be changed to "$CO_2$".

Signed and Sealed this

Thirteenth Day of September, 1994

Attest:

BRUCE LEHMAN

*Attesting Officer*     *Commissioner of Patents and Trademarks*